(12) United States Patent
Koshti et al.

(10) Patent No.: US 7,534,816 B2
(45) Date of Patent: May 19, 2009

(54) AMIDOBETAINES FOR ORAL CARE APPLICATIONS

(75) Inventors: Nirmal Koshti, Mumbai (IN); Bharat Parab, Mumbai (IN); Shubhangi Naik, Thane (IN)

(73) Assignee: Galaxy Surfactants Limited, Navi Mumbai, Maharashtra (IN)

( * ) Notice: Subject to any disclaimer, the term of this patent is extended or adjusted under 35 U.S.C. 154(b) by 340 days.

(21) Appl. No.: 11/327,202

(22) Filed: Jan. 6, 2006

(65) Prior Publication Data

US 2007/0004801 A1    Jan. 4, 2007

(51) Int. Cl.
*A01N 37/30* (2006.01)
*A61K 31/205* (2006.01)

(52) U.S. Cl. ......................... 514/554; 554/52
(58) Field of Classification Search ............... 554/52
See application file for complete search history.

(56) References Cited

U.S. PATENT DOCUMENTS

| 5,135,543 | A | | 8/1992 | Chan et al. | |
|---|---|---|---|---|---|
| 5,256,823 | A | | 10/1993 | Chan et al. | |
| 5,354,906 | A | * | 10/1994 | Weitemeyer et al. | 554/52 |
| 6,107,498 | A | * | 8/2000 | Maisonneuve et al. | 554/69 |
| 2006/0128596 | A1 | * | 6/2006 | Koshti et al. | 510/490 |

FOREIGN PATENT DOCUMENTS

| EP | 0658340 | 6/1995 |
|---|---|---|
| EP | 0764015 | 4/2000 |
| EP | 0692246 | 10/2001 |
| EP | 0910333 | 2/2002 |
| EP | 0966256 | 2/2002 |
| JP | 04134025 | 5/1992 |
| WO | 97/46217 | 12/1997 |
| WO | 01/70183 | 9/2001 |
| WO | 02/26203 | 4/2002 |

* cited by examiner

*Primary Examiner*—Deborah D Carr
(74) *Attorney, Agent, or Firm*—Volpe and Koenig, P.C.

(57) ABSTRACT

An aqueous composition for oral care application comprising solution of an amidobetaine of the following general Formula I is disclosed;

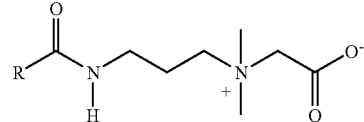

Formula I in which R is an alkyl of coconut fatty acids, preferably hydrogenated coconut fatty acids, or a fatty acid mixture group which, on the average, corresponds to coconut fatty acids, wherein the solution has a solids content of 36% by weight, a pH of 4.5 to 6, an alkylamidopropyldimethyl amine content of not more than 0.1% by weight, and a free fatty acid content less than 0.5% by weight, sodium chloride content of 6.0% max and dimethylaminopropylamino betaine (from N,N-dimethyl amino propyl 1,3-diamine (DMAPA) and monochloroacetic acid) content of 30 ppm max, free sodium monochloroacetic acid content of 5 ppm max and free N,N-dimethylamino propyl 1,3-diamine content of 5.0 ppm max.

1 Claim, No Drawings

AMIDOBETAINES FOR ORAL CARE APPLICATIONS

FIELD OF INVENTION

The present invention relates to an aqueous composition for oral care application. More particularly the invention relates to an aqueous oral care composition comprising solution of an amidobetaine of the Formula I

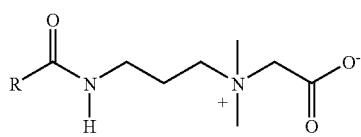

Formula I in which R is an alkyl of coconut fatty acids, preferably hydrogenated coconut fatty acids, or a fatty acid mixture group which, on the average, corresponds to coconut fatty acids.

BACKGROUND AND PRIOR ART

Alkylamidopropyl betaines in general and cocoamidopropyl betaine (CAPB, CAS 61789-40-0) in particular are known for their mildness and hence are very widely used in personal care and consumer products ["*Encyclopedia of conditioning rinse ingredients*" ed. A. L. L. Hunting, Micelle Press, London (1987), p. 125].

As a result of their superior performance, biodegradability and low toxicology profile, alkylamidopropyl betaines are used on a huge scale in cosmetic industry [X. Domingo, "*Amphoteric Surfactants*" ed. E. G. Lomax, Surfactant Science Series, Marcel Dekker Inc., New York, (1996), Vol. 59, p. 75 and J. G. Weers, J. F. Rathman, F. U. Axe, C. A. Crichlow, L. D. Foland, D. R. Scheuing, R. J. Wiersema and A. G. Zielske, *Langmuir*, 7, 854-867, (1991)].

A conventional commercial amidobetaine (CAPB) composition for personal care applications typically has the following composition:

| | |
|---|---|
| Water | 64% by weight |
| Betaine (Formula I) | 28–29% by weight |
| NaCl | 5–6% by weight |
| Glycerin | 0.3% by weight |
| Fatty acid | 0.5% by weight |
| Amidoamine (FormulaII) | ca. 0.3% by weight |
| Total solids content | ca. 36% by weight |

The solids content represents the sum of the components other than water. The synthesis of betaine involves a two-step process. In the first step, fatty acid (or methyl or glyceryl ester of fatty acid) is reacted with N,N-dimethylaminopropyl diamine (DMAPA) as depicted in eq-1 to yield alkylamidopropyldimethyl amine of Formula II. In the second step, alkylamidopropyldimethyl amine of step one is quaternized using sodium monochloroacetate (SMCA) in aqueous medium as shown in eq-2 to yield amidobetaine of Formula I. The proportions of amidobetaine and sodium chloride arise out of the stoichiometry of the reaction of the fatty amide (Formula II) with the tertiary amino group and sodium chloroacetate according to the equations given below.

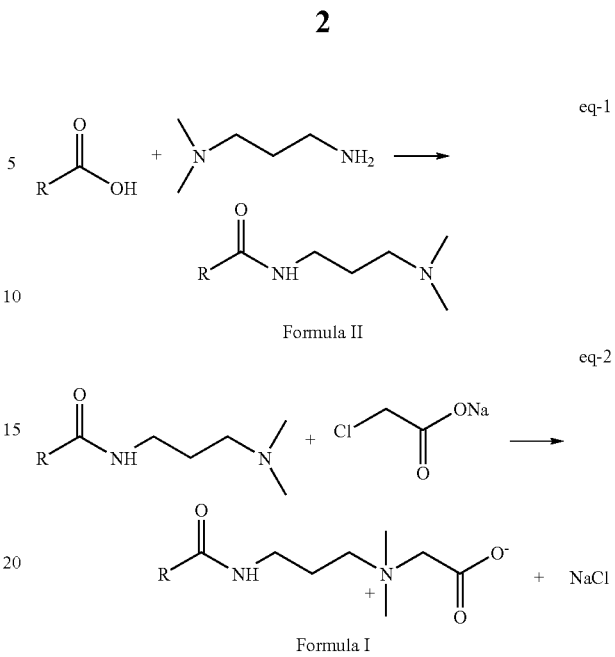

The free amidoamine content (Formula II) in the final amidobetaine arises from the incomplete quaternization and can be further reduced by an adapted stoichiometry and reaction procedure. It is usually present at around 0.3 to 0.5% in commercial betaine compositions. Small amounts of fatty acids (0.5%) in the amidobetaine composition results from synthesis of the amidoamine from the corresponding fatty acid and 3-N,N-dimethylaminopropyl amine (DMAPA). Further, a typical amidobetaine composition will contain glycerin if the amidoamine (Formula II) is synthesized from triglycerides (coconut or palm oil) and 3-N,N-dimethylaminopropyl amine.

Anionic surfactants like sodium lauryl sulphate (SLS), sodium cocoyl glycinate or sodium lauroyl sarcosinate are used in dentifrice applications. Sodium lauryl sulphate is the most commonly used anionic surfactant in the toothpaste formulation. A typical toothpaste formulation contains 0.5 to 2.5% of SLS for its foaming and surfactant action. However, these anionic surfactants are incompatible with the cationic ingredients of the formulation, especially with the quaternary ammonium type of antimicrobial molecules. Due to this incompatibility, one is compelled to use non-cationic antimicrobial agents that are either phenolic or halogenated molecules, e.g. triclosan or chlorhexidine. It is also pertinent to mention here that the most popular anionic surfactant for oral care applications, SLS, is actually a skin irritant and is generally not used in leave-on skin care preparations. SLS is also reported to cause significantly higher mucosal desquamation compared to amphoteric surfactants. (B. B. Herlofson and P. Barkvoll, Eur. J. Oral. Sci., 104, 21:6 (1996). However, despite these drawbacks the anionic surfactants are still being used since there are no other suitable alternatives. The cationic surfactants have incompatibility problem with other anionic ingredients. The nonionic surfactants are compatible with ionic ingredients but they do not foam. The amphoteric surfactants are free of this ionic incompatibility problem and hence they can be used with a cationic active in a formulation.

WO 97/46217, EP 0910333 and EP 0966256 describe mouthwash compositions comprising cationic antimicrobial cetyl pyridinium chloride and amphoteric cocoamidopropyl betaine.

According to EP 0764015, U.S. Pat. Nos. 5,256,823, and 5,135,543 quaternary ammonium compounds are found to be extremely useful in reducing oral bacteria and quite effective in preventing plaque and related periodontal diseases like gingivitis.

An amphoteric surfactant like CAPB has all the desired properties of being mild, biodegradable and foaming. It can replace anionic surfactants. It is also well known that combination of CAPB with an anionic like SLS results in foam boosting as well as reduces the latter's irritation potential. Hence an irritant like SLS can be fully or partially replaced by CAPB. There have been a number of instances in the prior art where CAPB is used for oral care applications (WO 0226203 (1992), JP 04134025 (1992), EP 658340 (1993), EP 692246 (1994), WO 9746217 (1997), JP 0912437 (1997), JP 0912175965 (1997). WO 0170183 (2001) and WO 0226203 are dentifrice compositions that are based on the amphoteric betaines and not on any anionic surfactant. However, CAPB suffers from a major disadvantage of being bitter in taste. The bitter taste can be overcome to some extent by adding more sweeteners. EP 658430 (1993) describes dentifrice compositions containing significant quantitities of amidobetaines wherein bitter after taste is significantly reduced using sweetening agents like thaumatin or sterioside in addition to sodium saccharine. This limits its use in oral care formulations and thus there is a great need for a 'suitable amphoteric surfactant' in oral care formulations. The inventors of the present invention have discovered that the inherent bitterness of CAPB composition stems from the original amidobetaine molecule (Formula I) as well as the other impurities present in the composition. The impurities of the composition are several times more bitter that the actual amidobetaine molecule and the bitterness of a typical composition can be reduced significantly, by overall reducing the impurities and byproducts, in particular the betaine formed from N,N-dimethylpropyl 1,3-diamine and monochloroacetic acid (Formula III) eq-3. This impurity has been identified as the bitterest of all the impurities and the by-products. In commercially available amidobetaine compositions for personal care the betaine of Formula III was found to be significantly high and there is no mention of its presence or its analysis in the prior art on this amphoteric surfactant.

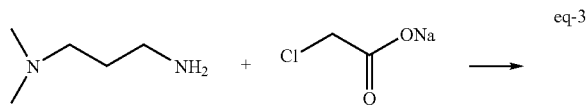

eq-3

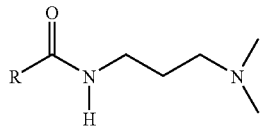

Formula III

SUMMARY OF THE INVENTION

According to one aspect of the present invention there is provided an amidobetaine composition comprising a betaine of the general Formula I,

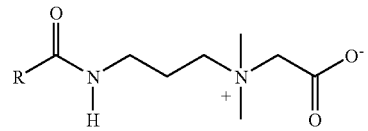

Formula I in which R is an alkyl group of coconut fatty acids, preferably hydrogenated coconut fatty acids, or a fatty acid mixture, which, on the average, corresponds to coconut fatty acids, an amidoamine of not more than 0.1% by weight, a free fatty acid less than 0.5% by weight, 0 to 4% by weight of glycerin, based on composition, less than 5 ppm of free sodium monochloroacetate and, less than 30 ppm of aminopropyl dimethylamino betaine (Formula III),

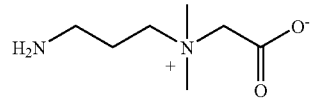

Formula III less than 5 ppm of free DMAPA wherein the composition has a solids content of at least 36% by weight and a pH of 4.5 to 6.

According to another aspect of the present invention there is provided a process for the preparation the said amidobetaine of Formula I by a two step procedure that controls the generation of impurities and the byproducts comprising quaternization of amidoamine of Formula II that contains less than 100 ppm of free N N-dimethyl propyl diamine (DMAPA), Formula II wherein, R is an alkyl group of coconut fatty acids, preferably hydrogenated coconut fatty acids, or a fatty acid mixture which, on the average, corresponds to coconut fatty acids alkyl group, with sodium salt of monochloroacetic acid at 80-85° C. while maintaining the pH between 7.5 to 8.5 by adding concentrated solution of sodium hydroxide till amidoamine content of the reaction mass has been brought down to 0.1% or less; raising the pH to between 10 to 10.5 and reaction is continued at a temperature of between 90-98° C.

for a period of 4-8 hours and thereafter adjusting the pH to 4.5 to 6.0 with phosphoric acid or citric acid or hydrochloric acid.

DETAILED DESCRIPTION OF THE INVENTION

Alkylamidopropyl betaines of the present invention for oral care have been achieved by a two step procedure that controls the generation of impurities and the byproducts. The amidobetaines of the present invention are produced by quaternizing the alkylamidopropyldimethylamine of Formula II with stoichiometric quantity of sodium monochloro acetate in aqueous medium. Thus, the first step in the synthesis of alkylamidopropyl betaine of the present invention is the synthesis of alkylamidopropyldimethyl amine.

Preparation of Alkylamidopropyldimethyl Amine of Formula II:

The alkylamidopropyldimethyl amine can be obtained by reacting stoichiometric amounts of fatty acids with 3-N,N-dimethylaminopropylamine or aminolysis of triglycerides with the same amine. Either route works very well and the amidification is normally done at 130-140° C. (shown in equation-1 (eq-1))

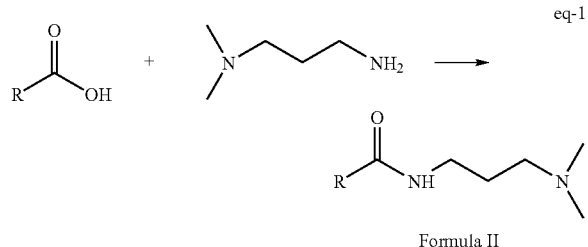

Formula II

Depending upon the fatty raw material used the amidoamine of Formula II may contain small amounts of unreacted triglyceride or fatty acids usually around 1% by weight. The progress of the reaction is monitored by estimating the free fatty acid. The amidoamine generated from triglyceride obviously has stoichiometric quantities of glycerin liberated. At the end of the reaction (free fatty acid content of less than 1.0%) the unreacted DMAPA is removed by washing the reaction mass by either water or even better, by brine solution. Another effective way of removing this small chain amine is by steam distillation. This is conveniently effected by passing steam in hot reaction mass at 120-170° C., preferably at 170° C. This operation is continued till the residual DMAPA content is brought down to less than 100 ppm in the reaction mass of amidoamine of Formula II (eq-1). Reaching of desired levels of free DMAPA is confirmed by ion chromatographic analysis using cation exchange column or by spectrophotometric analysis after converting the free amine into an UV-absorbing derivative [E. G. Frame, J. A. Russell, A. E. Whilhelmi, D. H. Rosenblatt, P. Hlinka & J. Eptein, J. Biol. Chem., 1949, 255, (1943)]. The low levels of free DMAPA in the alkylamidopropyl amine (Formula II) ensures that the corresponding betaine (Formula III) that gets formed in the second step always remains at levels less than 30 ppm in the final amidobetaine composition. Depending upon the original N,N-dimethylaminopropyl diamine content of fatty alkyl amidoamine it is possible to reduce the free DMAPA level as low as 15 ppm by passing the steam.

Preparation of Alkylamidopropyl Betaine of Formula I:

In the present invention the quaternization of amidoamine of Formula II is done by reacting 1.0 mole of amidoamine with 1.01 to 1.05 mole of sodium monochloroacetate at the temperature of 80-85° C. while maintaining pH between 7.5-8.0 by adding sodium hydroxide solution (45%). The amount of water that is usually taken in this step is to keep the solids content of the reaction mass around 38 to 40% by weight. The progress of the quaternization reaction is monitored by estimating the chloride ion liberated during the reaction as well as by estimating the unreacted amidoamine (shown in equation 2 (eq-2)). Both analytical parameters are used to ensure the completion of quaternization with free amidoamine around 0.1% by weight.

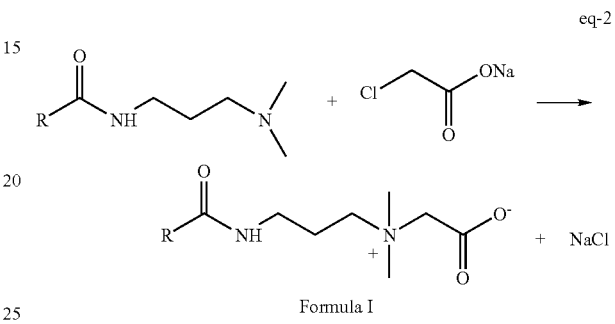

Formula I

Determination of free alkylamidopropyl amine from aqueous betaine composition is done by extracting and then titrating it against standard acid using potentiometry. Once the free alkylamidopropyl amine content of the reaction mass is confirmed to be less than 0.1% by weight then the temperature of the reaction mass (with the solids content 36% or above by weight) is raised from 85° C. to 95° C. and the pH is raised to 10-10.5 and the whole mass is stirred for four additional hours. This step is essential for the destruction of unreacted sodium monochloroacetate and to ensure that free sodium monochloroacetate is less than 5.0 ppm. This can also be conveniently done at higher temperature (100 to 140° C.) under pressure for quicker destruction of trace levels of sodium monochloroacetate. Free sodium monochloroacetate content is determined by ion chromatography of the 'solid phase extracted' betaine composition using anion exchange column. The betaine arising out of DMAPA (Formula III, eq-3) is conveniently analyzed by ion chromatography using anion exchange column. The synthesis and characterisation of betaine of Formula III and the chromatographic conditions are described in experimental section. Free DMAPA is analysed using cation exchange chromatography. Finally, on cooling, the pH of the reaction mass is adjusted to 4.5 to 6.5 by phosphoric acid or citric acid or hydrochloric acid. Adjustment of solids content to at least 36% gives clear, colorless, flowable amidobetaine composition.

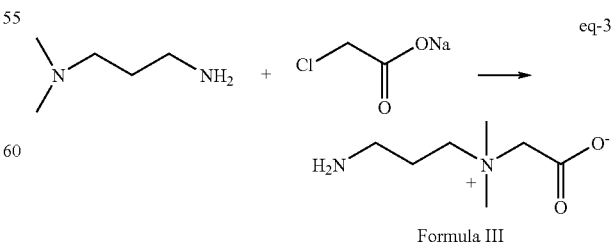

Formula III

The CAPB samples made from the above mentioned procedure were tested for 'taste' on a scale of 0 to 5, zero being the tasteless, without any bitterness and the score of 5 being the bitterest. The samples (0.25% active matter in water) were tested by a panel of 10 experts (with sensitive taste buds and high olfactory sense) that were specially trained for this 'tasting exercise'. The commercial amidobetaines from various suppliers world over for personal care applications were found to have score of 4 to 5. The samples of CAPB from ten different experiments generated as per the process and specifications described here in the present application had an average score of 1.0. This also established the repeatability and consistency of the improved process of the present invention (see Example I, Tables I and II).

The tooth paste formulation made from CAPB of the present invention was found to be of much superior taste compared to tooth paste formulation made from commercial CAPB for personal care (skin and hair) applications. The tooth paste formulations for the comparison purposes were made without any sweetener to enhance the effect of CAPB on the 'taste' of the formulation (see Example I, Table III)

The amidobetaines of improved taste can replace the irritant, expensive anionic surfactants like SLS partially or completely in an oral care formulation.

ADVANTAGES OF THE INVENTION

The amidobetaine composition of the present invention has the following advantages.
1) The process of the present invention gives an amidobetaine composition that is most suitable for oral care applications (mouth rinses and tooth pastes) due to its significantly less bitter taste compared to commercially available CAPB for personal care applications.
2) The amidobetaine of the present invention allows use of a number of powerful cationic antimicrobial agents in oral care formulations.
3) The amidobetaine of the present invention can replace anionic surfactants (that are irritant, expensive and incompatible with cationic actives) partially or totally.
4) Using the process of the present invention a high active, self preserving amidobetaine composition (45% solids minimum, 37% betaine content minimum) for oral care can also be made by incorporating other anionic surfactants like sodium lauroyl sarcosinate or sodium cocoyl glycinate (0.5 to 3%) that are very widely used in dental care products. (U.S. patent application Ser. No. 11/010,762 filed on Dec. 12$^{th}$ 2004, U.S. Pat. No. 5,354,906)
5) The process of the present invention yields amidobetaine composition with the lowest possible impurity level with less than 5.0 ppm of free sodium monochloroacetate and 3-N,N dimethylpropyldiamine and with less than 30 ppm of aminopropyl dimethylamino betaine, the totally undesirable impurities that contribute to the bitter taste of the product.

The following examples describe in detail the process and the amidobetaine composition of the present invention. These examples are by way of illustrations only and in no way restrict the scope of the invention.

EXAMPLES

Cocofattyacid alkylamidoamine is prepared from cocofattyacid and 3-N,N-dimethyl aminopropyldiamine. 3-N,N-Dimethylaminopropyldiamine is procured from BASF and sodium monochloroacetate is purchased from Clariant.

Example I

Process for Making Cocoamidopropyl Betaine Composition Containing 29% of Active Matter of Formula I and Total Solids of 36%.) (Experiment No. 1 of Table I)

The amidobetaine composition is synthesized by the following two steps.

Step I, Synthesis of Cocoalkylamido Propyl Dimethyl Amine

Hydrogenated cocofatty acid (1980 g, 9.16 mol) is reacted with N,N-dimethyl aminopropyldiamine (971 g, 9.52 mol) at 170° C. with continuous removal of water that is generated during the course of the reaction. The progress of the reaction is monitored by measuring the free fatty acid content of the reaction mass and is continued till fatty acid level reaches less than 1.0%. Steam is passed through this reaction mass at 170° C. for about 2-3 hours during which time free N,N-dimethylaminopropyldiamine level is reduced to <100 ppm. Free N,N-dimethylaminopropyldiamine content is determined by ion chromatography (the details are given below). Reaction mass is then cooled to room temperature and taken further for the second step of quaternization.

Step II, Synthesis of Cocoalkylamidopropyl Betaine

To a stirred mixture of cocofatty acid amidoamine from step I (300 g, 1.0 mole, tertiary nitrogen content of 4.61%, acid value 2.5, free N,N-dimethylaminopropyldiamine <100 ppm), and water (320 ml) under nitrogen at 65° C., an aqueous solution of sodium monochloroacetate (311.6 g, 40%, 1.07 moles) is added over a period of half an hour. The reaction mixture is stirred for 8 hours at 80-85° C. by maintaining the pH between 7.5 to 8.2 with sodium hydroxide (45% aqueous solution) and stirring is continued for 8 hours at 95° C. while maintaining pH between 10-10.5. The reaction mass is then cooled and the pH is adjusted to 4.5 to 5.5 with phosphoric acid to give a clear product (982 g). The composition of this amidobetaine solution is as given below.

| | |
|---|---|
| Solids | 35.5% |
| Amidobetaine (active matter) | 29.03% |
| NaCl | 5.35% |
| Fatty acid | 0.30% |
| Amidoamine | 0.09% |
| Sodium monochloroacetate | <5.0 ppm |
| Free N,N-dimethylaminopropyldiamine | <5.0 ppm |
| Aminopropyl dimethylamino betaine | <30 ppm |
| pH | 5.2 |

The ion exchange chromatography is performed on Dionex DX-500 ion chromatograph equipped with quaternary gradient pump and a conductivity detector. Background conductivity suppression is achieved by self-regenerating suppressors CSRS and ASRS-Ultra. Sodium monochloroacetate and aminopropyl dimethlamino betaine are analyzed by anion exchange chromatography (anion exchange column IonPac AS-12A with AG-12A guard column, mobile phase 10 mN NaOH, 1.5 ml/min). Amidobetaine samples are suitably diluted and solid phase extracted using octadecyl silane cartridges (Accubond from J & W) followed by passing through silver cartridge (OnGuard-Ag P/N 39637 from Dionex) before injecting them on the anion exchange column. Under these chromatographic conditions, the retention times for sodium monochloroacetate and aminopropyl dimethylamino betaine is 3.0 and 5.3 minutes respectively. Free 3-N,N-dimethylaminopropyldiamine is analyzed by cation exchange chromatography (cation exchange column IonPac CS-12A with CG-12A guard column, mobile phase 20 mN sulphuric acid, 1.0 ml/min). The synthesis of trifluoroacetate salt of betaine of Formula III required for chromatographic analysis is described below.

Synthesis of Boc Protected N,N-Dimethyl Aminopropyldiamine

To a cold solution of N,N-dimethyl aminopropyldiamine (2.0 g, 19.61 mmol) and triethylamine (3.96 g, 39.21 mmol) in THF (15 ml) a solution of t-butoxy carbonyl anhydride (4.27 g, 19.59 mmol) in THF (15 ml) is slowly added over 30 minutes and stirred for 4 hours at 50° C. The residue obtained after removal of solvent is dissolved in dichloromethane (30 ml) and washed with saturated solution of sodium bicarbonate (10 ml). Drying over sodium sulphate and evaporation of dichloromethane yields Boc protected N,N-dimethyl aminopropyldiamine as colourless liquid (3.41 g, 86%).

Synthesis of Boc Protected Betaine of N,N-Dimethyl Aminopropyldiamine

To a solution of Boc protected N,N-dimethyl aminopropyldiamine (2.0 g, 9.9 mmol) in t-butanol (15 ml) and water (1 ml), sodium monochloroacetate (1.154 g, 9.9 mmol) is added and the mixture is stirred for 8 hours at 80° C. The separated sodium chloride salt is filtered off. The filtrate is evaporated under reduced pressure to yield the product as pale yellow coloured viscous liquid (2.5 g, 97.3%). $^1$H NMR (CDCl$_3$, 300 MHz): δ 1.27 (s, 9H), 1.95-2.0 (m, unresolved broad signal, 2H), 3.15-3.17 (unresolved broad signal, 2H), 3.27 (s, 6H), 3.64 (unresolved broad signal, 2H), 3.94 (s, 2H).

Synthesis of Trifluoroacetate Salt of Betaine of N,N-Dimethyl Aminopropyldiamine To a stirred solution of Boc protected betaine of N,N-dimethyl aminopropyldiamine (2.5 g, 9.65 mmol) in dichloromethane (25 ml), trifluoroacetic acid (2.2 ml, 29 mmol) is added and stirred for 8 hours at room temperature. Evaporation of dichloromethane under reduced pressure yields trifluoroacetate salt of Boc protected betaine of N,N-dimethyl aminopropyldiamine (2.6, 98%) as off white solid. $^1$H NMR (D$_2$O, 300 MHz): δ 2.08-2.2 (m, 2H), 3.02-3.1 (t, 2H), 3.25 (s, 6H), 3.62-3.68 (t, 2H), 4.13 (s, 2H).]

The CAPB samples made from the above mentioned procedure are tested for taste on a scale of 0 to 5, zero being the tasteless, without any bitterness and five being the bitterest. The samples (10 ml of 0.25% active matter in water for 30 seconds in mouth) are tested by a panel of 10 experts (with sensitive taste buds and high olfactory sense) that are specially trained for this 'tasting exercise'. The analysis and the taste score are given in Table I.

The amidobetaine synthesis described in Example I is listed as experiment no. 1 in Table I. Nine other experiments have been performed and the results are given in Table I.

TABLE I

Analysis of amidobetaine samples of the present invention.

| Experiment No. | Total Solids % | Active Matter % | Amidoamine of Formula II % | Impurity of Formula III ppm | DMAPA ppm | SMCA ppm | Taste score |
|---|---|---|---|---|---|---|---|
| 1 | 35.5 | 29.03 | 0.09 | 25 | 1.3 | 1.5 | 1 |
| 2 | 36.03 | 29.1 | 0.08 | 16 | Nil | 1.5 | 1 |
| 3 | 35.9 | 29.10 | 0.06 | 22 | 1.3 | 2.4 | 1 |
| 4 | 35.9 | 29.00 | 0.09 | 12 | 3.0 | 3.0 | 1 |
| 5 | 36.1 | 29.06 | 0.06 | 14 | 1 | 1.0 | 1 |
| 6 | 36.0 | 29.1 | 0.09 | 11 | 2.1 | 2.0 | 1 |
| 7 | 36.06 | 29.1 | 0.06 | 12 | 1.2 | 3.0 | 1 |
| 8 | 35.70 | 29.00 | 0.06 | 4.5 | 1.2 | Nil | 1 |
| 9 | 36.00 | 28.92 | 0.05 | 18 | 1.3 | 1.4 | 1 |
| 10 | 35.90 | 29.01 | 0.06 | 13 | Nil | 1.3 | 1 |

On analysis of commercially available CAPB samples from global manufacturers (28-29% active) for personal care applications, the impurity of Formula III, aminopropyl dimethylamino betaine, is found to be in range of 500 to 3000 ppm whereas alkylamidoamine of Formula II is found to be in the range of 2000 to 5000 ppm (Table II).

TABLE II

Analysis of commercially available amidobetaine samples (CAPB)

| Sample Code | Total Solids % | Active Matter % | Amidoamine of Formula II % | Impurity of Formula III ppm | DMAPA ppm | SMCA ppm | Taste score |
|---|---|---|---|---|---|---|---|
| A | 35.5 | 29.4 | 0.40 | 4000 | 1.3 | 2.4 | 5 |
| B | 36.03 | 29.4 | 0.30 | 3500 | 2.8 | 4.4 | 4 |
| C | 35.9 | 29.14 | 0.46 | 800 | 1.3 | 3.0 | 4 |
| D | 35.9 | 29.23 | 0.32 | 1025 | 3.0 | 4.0 | 5 |
| E | 36.1 | 29.30 | 0.36 | 3050 | 3.0 | 6.0 | 5 |

The commercial samples of cocoamidopropyl betaine (global manufacturers) for personal care have been rated with a score of 4 to 5 uniformly since all of them have been found to be significantly bitter. As against this the cocoamidopropyl betaine samples of the present invention have been rated with a score of 1 uniformly.

A tooth paste formulation is made using amidobetaine of the present invention and compared with the tooth paste formulation made from commercially available amidobetaine for hair care and skin care. Both tooth pastes are used by a panel of seven individuals. The taste scores were recorded on a scale of 1 to 10. Taste while brushing teeth as well as after brushing was taken into consideration. The tooth pastes were made using the following formulation.

| | |
|---|---|
| Glycerin | 45% |
| Calcium carbonate | 2% |
| Sodium benzoate | 0.3% |
| CAPB | 2.0% |
| Water to make | 100% |

TABLE III

Taste scores for toothpastes

| Taste panelist no. → | 1 | 2 | 3 | 4 | 5 | 6 | 7 | Average taste score |
|---|---|---|---|---|---|---|---|---|
| Tooth paste with CAPB (commercial grade) | 6 | 10 | 10 | 6 | 6 | 6 | 7 | 7.2 |
| Tooth paste with CAPB (present invention) | 4 | 3 | 6 | 4 | 4 | 2 | 3 | 3.7 |

We claim:

1. An aqueous amidobetaine composition for oral care, comprising
from 28 to 30% by wt. of a betaine of the general Formula I,

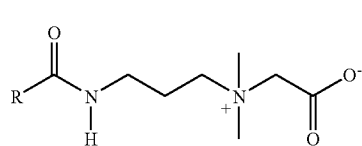

Formula I in which R is an alkyl group of coconut fatty acids,
an amidoamine of not more than 0.1% by weight,
a free fatty acid less than 0.5% by weight,
0 to 4% by weight of glycerin, based on composition,
less than 5 ppm of free sodium monochloroacetate and,
4.5 to less than 30 ppm of aminopropyl dimethylamino betaine of Formula III,

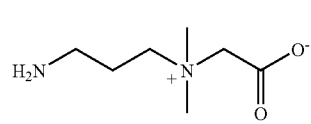

Formula III less than 5 ppm of free DMAPA wherein the composition has a solids content of at least 36% by weight and a pH of 4.5 to 6.

* * * * *